United States Patent [19]

Tischler et al.

[11] Patent Number: 4,760,086

[45] Date of Patent: Jul. 26, 1988

[54] N-ALKENYL-3-HYDROXYBENZO[B]THIOPHENE-2-CARBOXAMIDE DERIVATIVES AS DUAL CYCLOOXYGENASE AND LIPOXYGENASE INHIBITORS

[75] Inventors: Allan N. Tischler; Bruce E. Witzel, both of Westfield; Philippe L. Durette, New Providence; Kathleen M. Rupprecht, Cranford, all of N.J.; Timothy F. Gallagher, Harleysville, Pa.; Debra L. Allison, Scotch Plains; Marvin M. Goldenberg, Westfield, both of N.J.

[73] Assignee: Merck & Co., Inc., Rahway, N.J.

[21] Appl. No.: 705,115

[22] Filed: Feb. 27, 1985

[51] Int. Cl.[4] .................... A61K 31/38; C07D 333/62
[52] U.S. Cl. .................................... 514/443; 549/52; 549/54; 549/55
[58] Field of Search .................... 549/55, 53, 52, 54; 514/443

[56] References Cited

U.S. PATENT DOCUMENTS

| | | |
|---|---|---|
| 3,413,308 | 11/1968 | Bockstahler . |
| 3,862,320 | 1/1975 | Thominet . |
| 3,907,826 | 9/1975 | Stoss et al. . |
| 3,954,748 | 5/1976 | Thominet . |
| 4,260,779 | 4/1981 | Bernasconi et al. .................. 549/55 |

*Primary Examiner*—Alan Siegel
*Attorney, Agent, or Firm*—Theresa Y. Cheng; Michael C. Sudol

[57] ABSTRACT

N-Alkenyl-3-hydroxybenzo[b]thiophene-2-carboxamide derivatives have been prepared by:

(1) treating a substituted 2-halobenzoate with thioacetamide followed by N-alkenylation with appropriate agents, such as aldehydes, ketones, enol ethers, epoxides, acetals or ketals;

(2) treating a substituted thiosalicylate with an appropriately substituted haloacetamide, followed by dehydration; and (3) further synthetic modification of compounds prepared above.

These compounds have been found to be effective inhibitors of both cyclooxygenase and lipoxygenase and thereby useful in the treatment of pain, fever, inflammation, arthritic conditions, asthma, allergic disorders, skin diseases, cardiovascular disorders, psoriasis, inflammatory bowel disease, glaucoma or other prostaglandins and/or leukotriene mediated diseases. Furthermore, these compounds have been found to exhibit cytoprotective activity which does not involve the inhibition of gastric acid secretion but can be used at relatively low dosages for increasing the resistance of gastro-intestinal mucosa to strong irritants.

4 Claims, No Drawings

N-ALKENYL-3-HYDROXYBENZO[B]THIOPHENE-2-CARBOXAMIDE DERIVATIVES AS DUAL CYCLOOXYGENASE AND LIPOXYGENASE INHIBITORS

BACKGROUND OF THE INVENTION

This invention relates to benzothiophenes, particularly 3-hydroxybenzothiophenes having the unusual 2-enamido side chains, for example,

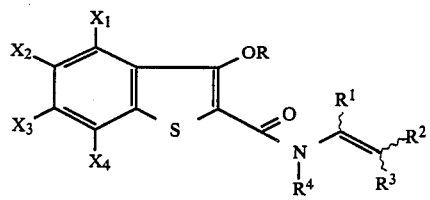

These novel benzothiophenes are found to be effective cyclooxygenase and 5-lipoxygenase inhibitors and are therefore useful in the treatment of inflammation and other prostaglandins leukotriene mediated diseases. They are also found to be useful in the treatment of elevated intraocular pressure especially when accompanied by pathological damage. Furthermore, they are useful cytoprotective agents.

Among various potent biological mediators derived from the oxygenation of arachidonic acid, prostaglandins and leukotrienes have been linked to various diseases. Notably, the biosynthesis of prostaglandins has been identified as a cause of inflammation, arthritic conditions (e.g., rheumatoid arthritis, osteoarthritis and gout), psoriasis, inflammatory bowel disease, and pain. Furthermore, the formation of leukotrienes has been connected to immediate hypersensitivity reactions and pro-inflammatory effects. It has been established that arachidonic acid undergoes oxygenation via two major enzymatic pathways:

(1) The pathway catalyzed by the enzyme cyclooxygenase; and
(2) The pathway catalyzed by the enzyme 5-lipoxygenase.

Interruption of these pathways by enzyme inhibition has been explored for effective therapy. For example, non-steroidal anti-inflammatory drugs (NSAID) such as aspirin, indomethacin and diflunisal are known cyclooxygenase inhibitors which inhibit the process wherein arachidonic acid is oxygenated via cyclooxygenase to prostaglandins and thromboxanes.

Recently, it has been observed that certain leukotrienes are responsible for diseases related to immediate hypersensitivity reactions such as human asthma, allergic disorders, and skin diseases. In addition, certain leukotrienes and derivatives thereof are believed to play an important role in causing inflammation (B. Samuelsson, *Science*, 220, 568 (1983); D. Bailey et al, *Ann. Rpts. Med. Chem.*, 17, 203 (1982)).

Conditions involving elevated intraocular pressures which are too high for normal function may result in irreversible loss of visual function. For example, glaucoma, if untreated, may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many $\beta$-adrenergic blocking agents are effective in reducing intraocular pressure. While many of these agents are effective in reducing intraocular pressure, they also have other characteristics, e.g. membrane stabilizing activity, that are not acceptable for chronic ocular use.

To be an effective and acceptable topical agent, for treating inflammation in the eye, or ocular hypertension related diseases such as glaucoma, the drug must not only penetrate the ophthalmic tissues to reach the active sites within the eye, but it must also be devoid of those side effects including irritation, allergic reaction and the like which would militate against long term administration.

With respect to the cytoprotective activity of the compounds of the present invention, it has been known that (1) gastric cytoprotection does not involve inhibition of gastric acid secretion. For example, protaglandin F2B does not inhibit gastric acid secretion, but it does induce gastric cytoprotection (S. Szabo et al., *Experimentia*, 38, 254, 1982); (2) lower effective dosages of cytoprotective agents are required than that of gastric acid inhibitors; and (3) the cytoprotective activity of a compound may be observed in both animals and man by noting the increased resistance of gastrointestinal mucosa to strong irritants. For example, animal studies have shown that cytoprotective compounds will prevent gastric lesions induced by oral administration of strong acids, strong bases, ethanol, hypertonic saline, etc.

DETAILED DESCRIPTION OF THE INVENTION

A. SCOPE OF THE INVENTION

The present invention relates to novel compounds of formula (I):

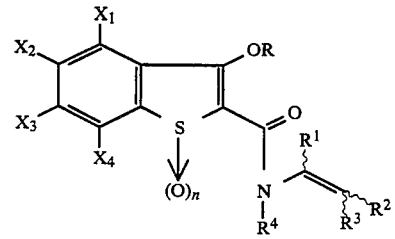

or a pharmaceutically acceptable salt thereof wherein R is
(a) H;
(b) loweralkyl, especially $C_{1-6}$ alkyl such as methyl, ethyl, i-propyl, n-propyl, t-butyl, n-butyl, i-pentyl, n-pentyl and n-hexyl;
(c) aryl especially $C_{6-14}$ aryl e.g., naphthyl, anthryl, phenyl or substituted phenyl of formula

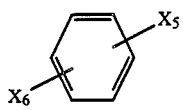

wherein X₅ and X₆ independently are:
(1) Q, where Q is H, loweralkyl especially $C_{1-6}$ alkyl, haloloweralkyl especially fluoro or chloro $C_{1-6}$ alkyl such as trifluoromethyl, phenyl or substituted phenyl, or naphthyl;
(2) halo especially chloro, fluoro, bromo or iodo;
(3) loweralkenyl especially $C_{2-6}$ alkenyl such as ethenyl and allyl;
(4) loweralkynyl especially $C_{2-6}$ alkynyl, for example, ethynyl or n-butynyl;
(5) —SQ;
(6) —OQ;
(7) —CHQCOQ¹, where Q is Q¹ and can be the same as or different from Q';
(8) —CHQCOOQ¹;
(10) —CH₂SQ or —CHQSQ¹;
(11) —CH₂OQ or —CHQOQ¹;
(12) —COQ;
(13) —COOQ;
(14) —OCOQ;
(15) —NQQ¹;
(16) —NQCOQ¹;
(17) —NQ(OQ¹);
(18) —NQ(SQ¹);
(19) —NQSO₂Q¹;
(20) —SO₂NQQ¹;
(21) —SOQ;
(22) —SO₂Q;
(23) —SO₃Q;
(24) —CN;
(25) —NO₂;
(26) —CONQQ';
(27) —NO;
(28) —CSQ;
(29) —CSNQQ';
(30) —CF₂SQ;
(31) —CF₂OQ;
(32) —NQCONHQ¹ or NQCONQ¹Q²;
(d) lowercycloalkyl especially $C_{3-6}$ cycloalkyl, e.g., cyclopropyl, cyclopentyl and cyclohexyl;
(e) haloloweralkyl especially halo $C_{1-6}$ alkyl, e.g. CF₃—, CHF₂—, C₂F₅—;
(f) heteroaryl or heteroaryl substituted with X₅ and X₆ especially pyridyl, pyrryl, furyl or thienyl wherein X₅ and X₆ are as previously defined;
(g) benzyl or substituted benzyl of formula

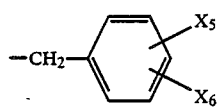

wherein X₅ and X₆ are as previously defined;
(h) loweralkynyl especially $C_{1-6}$ alkynyl such as —C≡CH; CH₃—C≡C—, or HC≡C—CH₂—;
(i) loweralkenyl especially $C_{1-6}$ alkenyl, such as CH₂=CH—, CH₃CH=CH—, CH₂=CHCH₂—, CH₃CH=CH—CH₂— or (CH₃)₂C=CH;
(j) phenylloweralkenyl of formula

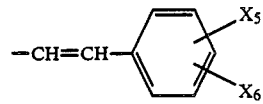

where X₅ and X₆ are as previously defined; or
(k) phenylloweralkynyl of formula

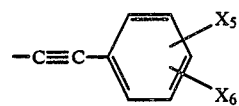

where X₅ and X₆ are as previously defined;
(l)

wherein R⁵ is R;
(m)

(n)

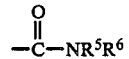

wherein R⁶ is R⁵ and can be the same as or different from R⁵;
(o)

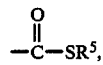

(p)

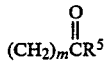

wherein m is 1 or 2;
(q) —(CH₂)ₘOR⁵;
(r)

(s) —(CH₂)ₘNR⁵R⁶; or
(t)

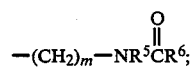

n is 0, 1 or 2;
X₁, X₂, X₃ and X₄ independently are
(a) R as previously defined; or
(b) X₅;
R¹, R² and R³ independently are
(a) R; or (b) R² and R³ joined together forming a ring of structure

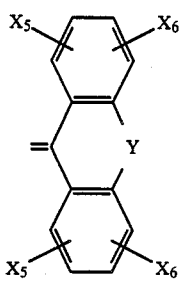

wherein X₅ and X₆ are as previously defined and Y is $(CH_2)_n$, O, S, SO, SO₂, NQ; or
(c) halo;
R⁴ is
(a) R; or
(b) $-CR^1=CR^2R^3$;
Preferably, a dual enzyme inhibitor of this invention is of formula:

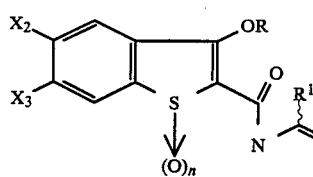

wherein X₂, X₃, R, R¹, R², R³, R⁴ and n are as previously defined.

More preferably, a dual enzyme inhibitor of this invention is formula:

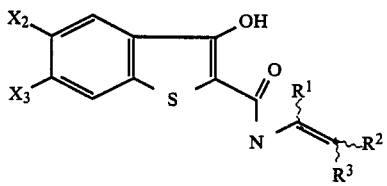

wherein X₂, X₃, R¹, R², R³ and R⁴ are as previously defined.

Even more preferably, a dual enzyme inhibitor of this invention is of formula:

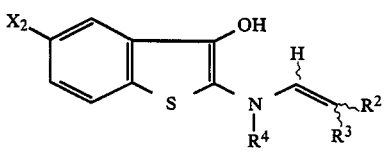

wherein
X₂ is
(a) H;
(b) loweralkyl;
(c) haloloweralkyl especially halo-$C_{1-6}$alkyl such as CF₃; or
(d) loweralkenyl especially $C_{2-6}$alkenyl; and
R² and R³ independently are:
(a) loweralkyl;
(b) phenyl or substituted phenyl;
(c) heteroaryl or substituted heteroaryl especially thienyl, furyl or pyrryl; and
R⁴ H or $-CH=CHR^2$.

The representative compounds of the present invention are those listed in the following tables:

TABLE I

| X₂ | R² | R³ | R⁴ | m.p. (°C.) |
|---|---|---|---|---|
| 5-CF₃ | 2-thienyl | phenyl | H | 207–208.5 |
| " | phenyl | 2-thienyl | H | 207–208.5 |
| " | phenyl | 2-thienyl | CH₃ | 192–194 |
| " | phenyl | phenyl | CH₃ | 147–150 |
| " | 2-thienyl | 4-CH₃S—phenyl | H | 164–165 |
| " | 2-(5-methyl-thienyl) | phenyl | H | 178–180 |
| " | 2-thienyl | 2-thienyl | H | 197–198.5 |
| " | 4-chloro-phenyl | phenyl | H | 186–189 |
| " | 4-fluoro-phenyl | phenyl | H | 201–202 |
| " | 4-methyl-phenyl | 4-methyl-phenyl | H | 218–220 |
| H | methyl | methyl | H | 213–215 (dec) |
| 5-CF₃ | 4-fluoro-phenyl | 4-fluoro-phenyl | H | 205–208 |
| " | 4-methoxy-phenyl | phenyl | H | 168–174 |
| " | 4-methoxy-phenyl | 4-methoxy-phenyl | H | 178–183 |
| " | 4-hydroxy-phenyl | 4-hydroxy-phenyl | H | |
| " | 2-furyl | phenyl | H | 160–162 |
| " | phenyl | 2-furyl | H | 156–158 |
| " | 2-furyl | 4-methyl-thiophenyl | H | |
| " | 2-(3-methyl-thioimida-zolyl) | phenyl | H | |
| " | phenyl | 4-methyl-thiophenyl | H | 157–159 |
| " | 4-methyl-thiophenyl | 4-methyl-thiophenyl | H | 213–214 |
| 5-CF₃ | phenyl | cyclohexyl | H | |
| " | phenyl | methyl | H | 207–211 |
| " | phenyl | benzyl | H | |
| " | Cl | Cl | H | 131–134 |
| " | phenyl | CF₃ | H | 123–125 |
| 4-CF₃ | phenyl | phenyl | H | |
| 5-F | " | " | H | 186–189 |
| 5,7-difluoro | " | " | H | 177–179 (dec) |
| 5-Cl | " | " | H | 245–246 |
| 4-CH₃O | " | " | H | 174–175 |
| 5-CH₃ | " | " | H | 200–201 |
| 5-CH₃ | 3-fluoro-phenyl | 3-fluoro-phenyl | H | |
| 5-CH₃ | phenyl | 4-methyl-phenyl | H | 199–203 |
| 5-CF₃ | phenyl | phenyl | H | 218–219 |
| 5-CF₃ | phenyl | phenylthio | H | 176–177 |
| 5-CF₃ | 4-methoxy-phenyl | 4-CH₃S—phenyl | H | |
| 5-phenyl | phenyl | phenyl | H | 185–187 |
| 5-(2,4-difluorophenyl) | " | " | H | 196–198 (dec) |
| 5-CH₃S | 2-thienyl | phenyl | H | |
| H | 2-thienyl | phenyl | H | |
| 6-CF₃CONH— | phenyl | 2-thienyl | H | |
| 6-CF₃ | 2-pyridyl | phenyl | H | |

TABLE I-continued

[Structure: 3-hydroxybenzo[b]thiophene-2-carboxamide with N-CHR—CH=CR²R³ substituent, X₂ on benzene ring]

| X₂ | R² | R³ | R⁴ | m.p. (°C.) |
|---|---|---|---|---|
| 6-CF₃ | phenyl | pyrryl | H | |
| 5-CF₃ | 4-fluoro-phenyl | 2-(5-methyl-thienyl) | H | 178.5–180 |
| 5-CF₃ | 4-methyl-phenyl | 2-thienyl | H | 163–170 |
| 7-CF₃ | 4-CH₃S—phenyl | 2-furyl | H | |
| 5-CF₃ | COOC₂H₅ | H | H | |
| 5-CF₃ | 4-CH₃SO—phenyl | phenyl | H | 220–223 (dec) |
| 5-CF₃ | 4-hydroxy-phenyl | phenyl | H | 197–201 |
| 5-CF₃ | 4-hydroxy-phenyl | 4-CH₃S—phenyl | H | 216–220 |
| 5-CF₃ | 4-CH₃S—phenyl | 2-(5-methyl-thienyl) | H | 156.5–160.5 |

TABLE II

[Structure: 3-hydroxybenzo[b]thiophene-2-carboxamide with N(CH=CHR²)(CH=CHR³)]

| X₂ | R² | R³ | m.p. (°C.) |
|---|---|---|---|
| 5-CF₃ | phenyl | phenyl | 165–167 |
| 5-CF₃ | p-fluoeo-phenyl | p-fluoro-phenyl | 196–198 |
| 5-Cl | phenyl | phenyl | 218–225 |
| H | COOC₂H₅ | COOC₂H₅ | 159(dec) |
| 5-phenyl | phenyl | phenyl | 173–175 |
| 5-(2,4-difluorophenyl) | phenyl | phenyl | 138–140 |
| 5-CF₃ | phenyl | 2-thienyl | |

TABLE II-continued

| X₂ | R² | R³ | m.p. (°C.) |
|---|---|---|---|
| 5-CF₃ | 2-thienyl | 2-thienyl | |
| H | phenyl | phenyl | 167–169 |

TABLE III

[Structure: 3-hydroxybenzo[b]thiophene-2-carboxamide with xanthene-type bridging group containing Y]

| X₁ | Y | m.p. (°C.) |
|---|---|---|
| H | S | 232–234 (dec.) |
| 5-CF₃ | S | |
| 5-CF₃ | SO | |
| 5-OCH₃ | SO₂ | |
| 5-F | O | |
| 6-CF₃ | NCH₃ | |

B. Preparation of the compounds of the invention

The compounds of the present invention are prepared from known starting materials via various procedures, for example, methods as defined below:

Method A—N-alkenylation

An appropriately substituted 3-hydroxybenzo[b] thiophene-2-carboxamide is reacted with an N-alkenylation reagent containing a carbonyl group or the equivalent thereof according to the following scheme:

[Structure of starting material: benzo[b]thiophene with X₁, X₂, X₃, X₄ substituents, 3-OH, 2-C(=O)NH₂, and (O)ₙ on S] +

"N—alkenylation Agent"
e.g.,
(a) R¹COCHR²R³
(b) HCOCHR²R³
(c) RºOCH=CR²R³ or RºSCH=CR²R³

Acid
H⁺

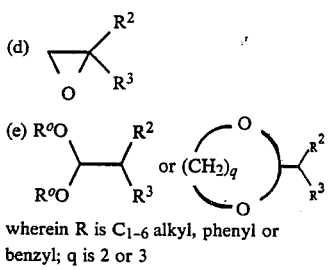

wherein R is $C_{1-6}$ alkyl, phenyl or benzyl; q is 2 or 3

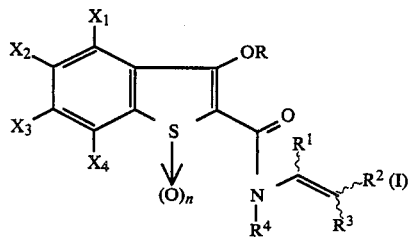

wherein the acid is a strong organic or inorganic acid or a mixture thereof, for example, arylsulfonic acid such as p-toluenesulfonic acid monohydrate, $H_2SO_4$, HCl, $H_3PO_4$, trifluoroacetic acid, alkylsulfonic acid such as methylsulfonic acid, acetic acid, trichloroacetic acid or the like.

EXAMPLE 1

5-Fluoro-3-hydroxy-N-(2,2-diphenylethenyl)benzo[b]-thiophene-2-carboxamide

Note: Steps A–C provide procedures for the preparation of 5-Fluoro-3-hydroxybenzo[b] thiophene-2-carboxamide, the starting material. Step D describes the N-alkenylation of [Method A, (a)]

Step A: Preparation of 0-2-Carbomethoxy-4-fluorophenyl dimethylthiocarbamate To a solution of methyl 5-fluorosalicylate (3.93 g, 23.1 mmol) in dry N,N-dimethylformamide (30 ml) was added sodium hydride (1.1 g, 50% oil dispersion). After hydrogen gas evolution had ceased, the mixture was cooled in an ice-bath, and dimethylthiocarbamoyl chloride (3.71 g, 30.0 mmol) was added. The mixture was stirred at 80° C. for one hour, cooled, and poured into water (100 ml). The product was extracted with diethyl ether (2x), and the combined organic extracts were washed with water, 5% aqueous potassium hydroxide, water, dried (sodium sulfate), and evaporated. The solid obtained was recrystallized from diethyl ether-hexane to afford 3.16 g (53%) of 0-2-carbomethoxy-4-fluorophenyl dimethylthiocarbamate. The 90 MHz NMR spectrum in chloroform-d was in accord with the desired structure.

Step B: Preparation of S-2-Carbomethoxy-4-fluorophenyl dimethylthiocarbamate 0-2-Carbomethoxy-4-fluorophenyldimethylthiocarbamate (2.41 g) was heated at 240° C. under a nitrogen atmosphere for 45 minutes and cooled. The product was purified by chromatography on a column of silica gel (Merck β7734, elution with 3:1 hexanediethyl ether) to yield 1.29 (53.5%) S-2-carbomethoxy-4-fluorophenyl dimethylthiocarbamate. The 90 MHz NMR spectrum in chloroform-d was in accord with the desired structure.

Step C: Preparation of 5-Fluoro-3-hydroxybenzo[b]-thiophene-2-carboxamide

To a solution of S-2-carbomethoxy-4-fluorophenyl-dimethylthiocarbamate (1.29 g, 5.0 mmol) in dry methanol (25 ml) was added sodium methoxide (270 mg, 5.0 mmol). The mixture was stirred at reflux temperature for 4 hours under a nitrogen atmosphere, at which time additional sodium methoxide (540 mg) and 2-chloroacetamide (468 mg, 5.0 mmol) were added. The mixture was stirred at reflux temperature under nitrogen for 1 hour then cooled. Addition of water (18 ml) and acetic acid (1.2 ml) to the mixture resulted in precipitation of the product, which was filtered, washed with 1:2 methanol-water (20 ml), hexane, and then dried in vacuo to yield 773 mg (73%) of 5-fluoro-3-hydroxybenzo[b]thiophene-2-carboxamide, m.p. 235°–240° C. (dec.).

Step D: Preparation of 5-Fluoro-3-hydroxy-N-(2,2-diphenylethenyl)benzo[b]-thiophene-2-carboxamide To a solution of 5-fluoro-3-hydroxybenzo[b]-thiophene-2-carboxamide (400 mg, 1.89 mmol) in hot toluene (35 ml) were added diphenylacetaldehyde (577 mg, 2.84 mmol) and p-toluenesulfonic acid monohydrate (25 mg). The reaction mixture was stirred at reflux temperature for 2 hours with azeotropic removal of water, cooled, and evaporated under diminished pressure. The solid obtained was recrystallized from diethyl ether-hexane to yield 604 mg (82%) of 5-fluoro-3-hydroxy-N-(2,2-diphenylethenyl)benzo[b]thiophene-2-carboxamide, m.p. 186°–189° C.

EXAMPLE 2

N-[2-(2-Furyl)-2-phenylethenyl]-3-hydroxy-5-trifluoromethylbenzo[b]thiophene-2-carboxamide

[Method A, (c)]

To a solution of 3-hydroxy-5-trifluoromethylbenzo[b]thiophene-2-carboxamide (1.7 g, 6.5 mmol) in hot toluene (100 ml) were added a solution of 1-methoxy-2- phenyl-2-(2-furyl)-ethylene (E,Z-mixture) (1.6 g, 8.7 mmol) in toluene (10 ml), water (about 10 drops), and p-toluenesulfonic acid monohydrate (150 mg). The reaction mixture was stirred at reflux temperature for 30 minutes, cooled and filtered to remove unreacted carboxamide. The filtrate was washed with saturated sodium hydrogencarbonate solution, dried (sodium sulfate), and evaporated. The resulting dark red syrup was applied to a column of silica gel (Merck β7734, packed as a slurry in 1:1 dichloromethane-hexane). Elution with 1:1 dichloromethane-hexane afforded, after evaporation of the appropriate fractions, the pure, predominant, more mobile geometric isomer (by TLC) of N-[2-(2-furyl)2-phenylethenyl]-3-hydroxy-5-trifluoromethylbenzo[b]thiophene-2-carboxamide as a yellow-orange solid in 18.4% yield (513 mg); m.p. 171°–173° C. (dec.). The less mobile isomer (by TLC) was also isolated as a yellow-orange solid; m.p. 156°–158° C. (dec.).

EXAMPLE 3

3-Hydroxy-N-[2-(4-methoxyphenyl)-2-phenylethenyl]-5-trifluoromethylbenzo[b]thiophene-2-carboxamide

[Method A, (b)]

To a solution of 3-hydroxy-5-trifluoromethylbenzo[b]thiophene-2-carboxamide (300 mg, 1.15 mmol) in hot toluene (30 ml) were added 2-(4-methoxy-phenyl)-2-phenylacetaldehyde (390 mg, 1.72 mmol) and p-toluenesulfonic acid monohydrate (20 mg). The reaction mixture was stirred at reflux temperature for one hour, with azeotropic removal of water, cooled, and evaporated under diminished pressure. The resulting yellow solid was dissolved in diethyl ether, the solution filtered through Celite, and the filtrate evaporated. Recrystallization of the solid from diethyl ether-hexane afforded pure 3-hydroxy-N-[2-(4-methoxyphenyl)-2-phenylethenyl]-5-trifluoromethylbenzo[b]thiophene-2-carboxamide; yield 458 mg (85%); m.p. 168°–174° C.

EXAMPLE 4

3-Hydroxy-N-[2,2-di(4-hydroxyphenyl)ethenyl]-5-trifluoromethylbenzo[b]thiophene-2-carboxamide

[Method A (b)]

Step A: Preparation of
3-Hydroxy-N-[2,2-di(4-methoxyphenyl)ethenyl]-5-trifluoromethylbenzo[b]thiophene-2-carboxamide To a solution of 3-hydroxy-5-trifluoromethylbenzo[b]thiophene-2-carboxamide (300 mg, 1.15 mmol) in hot toluene (30 ml) were added 2,2-di-(4-methoxyphenyl)acetaldehyde (380 mg, 1.48 mmol) and p-toluenesulfonic acid monohydrate (20 mg). The reaction mixture was stirred at reflux temperature for one hour with azeotropic removal of water, cooled, and evaporated. Trituration of the residue with diethyl ether gave a yellow solid that was filtered, washed with ether, and dried in vacuo; to yield 453 mg (79%) of 3-hydroxy-N-[2,2-di(4-methoxyphenyl)ethenyl]-5-trifluoromethylbenzo[b]-thiophene-2-carboxamide, m.p. 178°–183° C.

Step B: Preparation of
3-Hydroxy-N-[2,2-di-(4-hydroxyphenyl)ethenyl]-5-trifluoromethylbenzo[b]thiophene-2-carboxamide To a solution of 3-hydroxy-N-[2,2-di-(4-methoxyphenyl)ethenyl]-5-trifluoromethylbenzo[b]thiophe ne-2-carboxamide (200 mg) in dichloromethane (30 ml) cooled to −50° C. was added dropwise with stirring N boron tribromide in dichloromethane (2.9 ml). The reaction mixture was stirred at −50° C. for one hour, then the temperature allowed to rise to 0° C., and the reaction quenched by pouring into ice-saturated sodium hydrogencarbonate solution. The yellow solid that separated out was filtered, washed thoroughly with hexane and dried in vacuo to yield 104 mg (55%) of 3-hydroxy-N-[2,2-di-(4-hydroxyphenyl)ethenyl]-5-trifluoromethylbenzo[b]thiophene-2-carboxamide; m/z 471 (M+).

EXAMPLE 5

3-Hydroxy-N-[2-phenyl-2-p-(methylthio)phenyl]ethenyl-5-trifluoromethylbenzo[b]thiophene-2-carboxamide

[Method A, (b)]

p-Toluenesulfonic acid monohydrate (200 mg) was added to a mixture of 3-hydroxy-5-trifluoromethylbenzo[b]thiophene-2-carboxamide (3.9 g, 0.015 mol) and α-(p-methylthiophenyl)phenylacetaldehyde (4.9 g, 0.020 mol) in toluene (100 ml). The reaction mixture was heated to reflux for 5 hours utilizing a Dean-Stark trap to collect any water formed during reaction. The solution was concentrated and the residue was subjected to column chromatography on silica gel (E. Merck, α7734), eluting with 1:1 dichloromethane/hexane. Concentration of the fractions containing the product followed by trituration of the residue with light petroleum ether gave 3-hydroxy-N-[2-phenyl-2-(4-methylthio)phenyl]ethenyl5-trifluoromethylbenzo[b]-thiophene-2-carboxamide as a yellow solid; yield 5.1 g (70%). M.p. of the mixture of isomers, 142°–152° C.

EXAMPLE 6

N-[2-Phenyl-2-(2-thienyl)]ethenyl-3-hydroxy-5-trifluoromethylbenzo[b]thiophene-2-carboxamide

[Method A, (c)]

A stirred mixture of 3-hydroxy-5-(trifluoromethyl)-benzo[b]thiophene-2-carboxamide (10 g, 0.038 m), 1-methoxy-2-phenyl-2-(2-thienyl)ethene (0.038 m) (prepared from 2-benzoylthiophene and (methoxymethyl)-triphenylphosphonium chloride via standard Wittig reaction; see G. Wittig and E. Krauss, *Angew. Chem.*, 71 127 (1959)) and toluene (350 ml) was covered with a nitrogen atmosphere and set in an oil-bath at 110° C. and rising. After 10 minutes, water (0.05 ml) and p-toluenesulfonic acid hydrate (0.5 g) were added, and the mixture refluxed until starting materials were consumed (ca. 1.5 hours).

Column chromatography (silica gel) of the concentrated reaction mixture, using a methylene chloride-hexane (1:1) system as eluant, followed by ether trituration of the resulting yellow solid yielded N-[2-phenyl-2-(2-thienyl)]ethenyl-3-hydroxy-5-trifluoromethylbenzo[b]thiophene-2-carboxamide (a eutectic mixture of cis and trans isomers), m.p. 207°–208.5° C.

Purification of
N-[2-phenyl-2-(2-thienyl)]ethenyl-3-hydroxy-5-trifluoromethyl]benzo(b)thiophene-2-carboxamide Step A: Preparation of
N-[2-Phenyl-2-(2-thienyl)]-ethenyl-3-benzoyloxy-5-(trifluoromethyl)benzo[b]thiophene-2-carboxamide A solution of N-[2-phenyl-2-(2-thienyl)]ethenyl-3-hydroxy-5-(trifluoromethyl)benzo[b]thiophene-2-carboxamide (11.2 g, 0.025 m) in 200 ml dry pyridine was cooled in an ice-bath, and benzoyl chloride (3.3 ml, 0.028 m) added dropwise over one minute. The stirred solution was allowed to warm to room temperature.

When thin-layer chromatography analysis showed no starting material remaining, the solution was added to a stirred mixture of ice-water-methylene chloride-and hydrochloric acid (conc'd, 210 ml), and the washed methylene chloride layer concentrated in vacuo to 13.8 g benzoate mixture.

Purification via chromatography (silica gel) on a Waters Prep LC-500A, using benzene as eluant, gave two isomeric benzoates:
Isomer A, m.p. 194°–196° C., and
Isomer B, m.p. 185°–187° C.

Step B: Preparation of pure N-[2-Phenyl-2-(2-thienyl)]ethenyl-3-hydroxy-5-trifluoromethyl-benzo[b]thiophene-2-carboxamide Applying standard, rapid low temperature basic hydrolysis of each individual benzoate obtained in Step A, there are obtained the pure isomeric N-[2-phenyl-2-(2-thienyl)]ethenyl-3-hydroxy-5-trifluoromethylbenzo[b]-thiophene-2-carboxamide:
Isomer A, m.p. 203°–205° C., and
Isomer B, m.p. 208°–210° C.

Following similar procedures as described above in Steps A and B, other O-derivatives of N-[2-phenyl-2-(2-thienyl)]ethenyl-3-hydroxy-5-trifluoromethylbenzo[b]-thiophene-2-carboxamide including propionates, methoxybenzoates, pivaloates or the like were prepared.

EXAMPLE 7

3-Hydroxy-N-[2'-p-(methylthio)phenyl-2'-p-(methoxy)-phenyl]ethenyl-5-trifluoromethylbenzo[b]thiophene-2-carboxamide

[Method A, (d)]

p-Toluenesulfonic acid monohydrate (10 mg) was added to a mixture of 3-hydroxy-5-trifluoromethylbenzo[b]thiophene-2-carboxamide (0.35 g, 1.3 mmol) and 1-p-(methoxy)phenyl-1-p-(methylthio)phenyl-1,2-epoxyethane (0.50 g, 1.8 mmol) in toluene (10 ml). The mixture was heated to reflux for 3 hours utilizing a Dean-Stark trap to collect the water formed during reaction. The solution was cooled and concentrated. The residue was subjected to flash column chromatography on silica gel (E. Merck β89385), eluting successively with 1:1 dichloromethane/hexane, 100:100:2 dichloromethane/hexane/acetic acid and 100:1 dichloromethane/acetic acid. Fractions containing the product were evaporated and the residue was triturated with light petroleum ether to give 3-hydroxy-N-[2'-p-(methylthio)phenyl-2'-p-(methoxy)phenyl]ethenyl-5-trifluoromethylbenzo[b]-thiophene-2-carboxamide as a yellow solid; yield 0.40 g (60%).

EXAMPLE 8

N,N-bis(p-Fluorostyryl)-3-hydroxybenzo[b]thiophene-3-carboxamide

[Method A, (e)]

Under a nitrogen atmosphere, a stirred mixture of 3-hydroxybenzo[b]thiophene-2-carboxamide (0.48 g, 0.0025 m), p-fluorophenylacetaldehyde diethyl acetyl (1.1 g, 0.005 m; prepared from p-fluorobenzyl chloride and triethylorthoformate via the procedure of Fr. No. 1,327,160) and toluene (25 ml) was set in an oil-bath at 110° C. (and rising). After 10 minutes, water (2 drops) and p-toluenesulfonic acid (50 mg) was added, and the mixture refluxed until thin-layer chromatography analysis showed no starting materials remaining. Chromatography (silica gel; methylene chloride-hexane 1:1 as eluant) of the concentrated reaction mixture yielded N,N-bis(p-fluorostyryl)-3-hydroxybenzo[b]thiophene-3-carboxamide as a yellow solid, m.p. 149.5°–151° C.

EXAMPLE 9

3-Hydroxy-N,N-di-(2-phenylethenyl)-5-trifluoromethyl-benzo[b]thiophene-2-carboxamide

[Method A, (b)]

p-Toluenesulfonic acid monohydrate (55 mg) was added to a mixture of 3-hydroxy-5-trifluoromethylbenzo[b]thiophene-2-carboxamide (1.1 g, 4.4 mmol) and phenylacetaldehyde (1.0 g, 8.8 mmol) in toluene (25 ml). The reaction mixture was heated to reflux for 0.5 hours utilizing a Dean-Stark trap to collect the water formed during reaction. The solution was cooled, filtered and the filtrate concentrated. The residue was subjected to column chromatography on silica gel (E. Merck β7734), eluting with 1% acetic acid in 5:1 hexane/ether. Fractions containing the product were concentrated and the residue was recrystallized from cyclohexane to give 0.31 g (21%) of 3-hydroxy-N,N-di-(2'-phenylethenyl)-5-trifluoromethylbenzo[b]thiophene-2-carboxamide, m.p. 165°–167° C.

Method B—Dehydration

By this method, an appropriately substituted thiosalicylate is reacted with a haloacetamide to give the ring closure product:

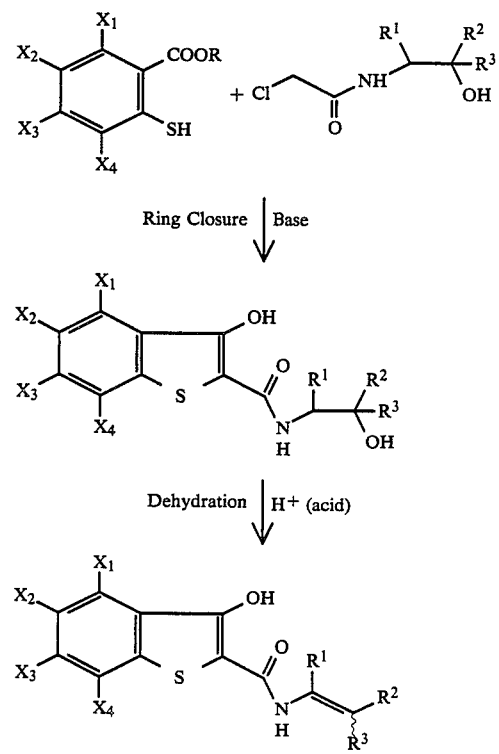

wherein acid is as previously defined; and base is a strong base, for example, NaOCH3, LiO(n-Bu), NaOt-Bu, KOCH3, etc.

EXAMPLE 10

N-(1,1-Diphenyl-1-propen-2-yl)-3-hydroxy-5-tri-fluoromethylbenzo[b]thiophene-2-carboxamide Step A: Preparation of 2,2-Diphenyl-3-methyloxirane A solution of 2.00 g (10.3 mmol) 1,1-diphenylpropene and 2.09 g (10.4 mmol) 85% m-chloroperbenzoic acid in 15 ml dichloromethane was stirred in the dark at room temperature for 4 hours. The mixture was partitioned between dichloromethane and saturated $K_2CO_3$ solution and the organic layer was washed with brine and dried over $Na_2SO_4$. This was concentrated to give 2.14 g (98%) of 2,2-diphenyl-3-methyloxirane as a colorless oil.

Step B: Preparation of 2-Azido-1,1-diphenylpropanol

A solution of 9.35 g (44.5 mmol) 2,2-diphenyl-3-methyloxirane and 9.00 g (138 mmol) $NaN_3$ in 100 ml of 2:1 N,N-dimethylformamide-water was heated at reflux for 72 hours. The solution was concentrated and the residue was partitioned between ether and water. The ether layer was washed with $NaHCO_3$, then water, dried over $Na_2SO_4$ and concentrated. HPLC (5% EtOAc-hexane) afforded 7.86 g (70%) of 2-azido-1,1-diphenylpropanol as a clean oil.

Following the similar procedure as described above, there was obtained in 79% yield 2-azido-1,2-diphenylethanol, m.p. 59°–60° C.

Step C: Preparation of 2-Amino-1,1-diphenylpropanol

A suspension of 1.10 g (4.34 mmol) 2 and 0.200 g PdO in 10 ml of 1:1 ethyl acetate-ethanol was shaken under 45 psi $H_2$ at room temperature for 2 hours. The mixture was filtered through Celite and concentrated to a white solid that was crystallized from ethyl acetate to afford 0.960 g (97%) of 2-amino-1,1-diphenylpropanol as white needles, m.p. 44°–45° C.

Following substantially the same procedure as described above, there was obtained in 95% yield, 2-amino-1,2-diphenylethanol, m.p. 295°–296° C.

Step D: Preparation of 2-(2-Chloroacetylamino)-1,1-diphenylethanol

A solution of 0.33 ml (0.975 g, 4.2 mmol) chloroacetyl chloride in 10 ml THF was cooled to 0° C. To this was added a solution of 0.8 g (3.98 mmol) 2-amino-1,1-diphenylpropanol and 0.6 ml (0.436 g, 4.31 mmol) triethylamine in 10 ml THF. The resulting solution was stirred at 0° C. for 2 hours before it was filtered and the residue washed with THF. The combined filtrate was concentration and the residue crystallized from ethyl acetate-hexane to afford 0.986 g (78%) of 2-(2-chloroacetylamino)-1,1-diphenylethanol, m.p. 178°–180° C.

Step E: Preparation of N-1,1-Diphenyl-1-hydroxy-2-propyl)-3-hydroxy-5-trifluoromethylbenzo[b]-thiophene-2-carboxamide A solution of 1.00 g (3.68 mmol) of 2-(2-chloroacetylamino)-1,1-diphenylethanol and 0.591 g (2.64 mmol) of methyl-(5-trifluoromethyl)thiosalicylate in 10 ml of 0.5M NaOMe-methanol was stirred at room temperature for 20 minutes. Then 10 ml of 2M NaOMe-methanol was added and the mixture was heated at reflux for 2 hours. The solution was cooled, acidified with glacial acetic acid and diluted with 100 ml of water. The precipitate was collected and dried to afford 0.963 g (80%) of white powder, m.p. 129°–130° C.

Applying similar procedures as described above in Steps C-E, there were prepared:

(a) N-(1,2-diphenyl-2-hydroxyethyl)-3-hydroxy-5-trifluoromethylbenzo[b]thiophene-2-carboxamide 80%, m.p. 168°–170° C.;

(b) N-(2-furyl-2-hydroxy-2-phenylethyl)-3-hydroxy-5-trifluoromethylbenzo[b]thiophene-2-carboxamide m.p. 166°–168° C.;

(c) N-(2-thienyl-2-hydroxy-2-phenylethyl)-3-hydroxy-5-trifluoromethylbenzo[b]thiophene-2-carboxamide m.p. 177°–179° C.

Step F: Preparation of N-(1,1-diphenyl-1-propen-2-yl)-3-hydroxy-5-trifluoromethylbenzo[b]thio-phene-2-carboxamide A suspension of 0.150 g (0.318 mmol) of N-(1,1-diphenyl-1-hydroxy-2-propyl)-3-hydroxy-5-trifluoro methylbenzo[b]thiophene-2-carboxamide and 2 mg of p-toluenesulfonic acid monohydrate in 15 ml toluene was heated at reflux with a Dean-Stark trap.

The solution was cooled, neutralized with solid $Na_2CO_3$, and evaporated. The residue was chromatographed on silica gel (20% ethylacetatehexane) to afford 0.118 g (82%) of N-(1,1-diphenyl1-propen-2-yl)-3-hydroxy-5-trifluoromethylbenzo[b]thiophene-2-carboxamide as a pale yellow needles (after recrystallization from hexane), m.p. 139°–140° C.

Following similar procedures as described above, there were prepared:

(a) N-(1,2-diphenylethenyl)-3-hydroxy-5-trifluoromethylbenzo[b]thiophene-2-carboxamide (66%), m.p. 143°–145° C.;

(b) N-(2-furyl-2-phenylethenyl)-3-hydroxy-5-trifluoromethylbenzo[b]thiophene-2-carboxamide (56%), m.p. 159°–161° C.;

(c) N-(2-thienyl-2-phenylethenyl)-3-hydroxy-5-trifluoromethylbenzo[b]thiophene-2-carboxamide (19%), m.p. 155°–160° C.

Method C - Derivatization

By this method, a 3-hydroxy-benzo[b]thiophene-2-carboxamide is modified to another. The following Examples serve to illustrate the general procedures.

EXAMPLE 11

3-Hydroxy-N-[2'(p-hydroxyphenyl)-2'-phenyl]ethenyl-5-trifluoromethylbenzo[b]thiophene-2-carboxamide A solution of boron tribromide in dichloromethane (0.88 ml of 1 m solution) was added to a solution of 3-hydroxy-N-[2'-p(methoxy)phenyl-2'-phenyl]ethenyl-5-trifluoromethylbenzo[b]thiophene-2-carboxamide (0.050 g, 0.11 mmol) in dichloromethane (10 ml) at −78° under a nitrogen atmosphere. The reaction mixture was permitted to gradually warm to −10° over the course of 4 hours. The cold solution was poured into water and the layers were separated. The organic phase was washed with those portions of water, saturated aqueous sodium chloride, dried (sodium sulfate) and concentrated. The residue was recrystallized from ether/petroleum ether to give 3-hydroxy-N-[2'(p-hydroxyphenyl)-2'-phenyl]ethenyl-5-trifluoromethylbenzo[b]thiophene-2-carboxamide as a yellow solid 0.017 g (34%), m.p. 197°–201° C.

EXAMPLE 12

3-Methoxy-N-methyl-N-(2,2-diphenyl)ethenyl-5-trifluoromethylbenzo[b]thiophene-2-carboxamide To a stirred solution of 0.50 g (1.139 mM) of 3-hydroxy-5-trifluoromethylbenzo[b]thiophene-2-carboxamide in 10 ml of DMSO was added with slight cooling, 55 mg (2.28 mM-2 eqv) of 97% NaH and the mixture stirred for 1 hour at R.T. under a nitrogen atmosphere. To this mixture was added 0.3248 (2.28 mM-2 eqv) of methyliodide in one portion and the mixture heated at 50° C. for 2 hours. The reaction mixture was poured into 100 ml of a ice-$H_2O$ mixture, collected the precipitate, washed with water, air dried to give 0.50 g (94%) of 3-methoxy-N-methyl-N-(2,2-diphenyl)ethenyl-5-trifluoromethylbenzo[b]thiophene-2-carboxamide as a yellow solid. M/z 467 (M+).

EXAMPLE 13 (0-Demethylation)

3-Hydroxy-N-methyl-N-(2,2-diphenyl)ethenyl-5-trifluoromethylbenzo[b]thiophene-2-carboxamide To a stirred solution of 3-methoxy-5-trifluoromethyl-benzo[b]thiophene-2-carboxamide in 10 ml of methylene chloride cooled to −78° C. was added dropwise a 1 molar solution of boron tribromide/$CH_2Cl_2$ over 1 minute under a nitrogen atmosphere. After 5 minutes at −78° C. the solution was warmed to 0° C. for 15 minutes, 10 ml of $H_2O$ was added and the mixture stirred 5 minutes. Separated the methylene chloride layer, dried, and concentrated down to give 0.448 g (92%) of a crude yellow solid. The crude solid was separated on several prepared TLC plates in 10% EtOAc/Hexane to give 0.109 g (23%) of 3-hydroxy-N-methyl-N-(2,2-diphenyl)ethenyl-5-trifluoromethylbenzo[b]thiophene-2-carboxamide as a pale pink solid having m.p. 147°–150° C.

Following similar procedures as described above, there was prepared 3-hydroxy-N-methyl-N-(2-phenyl-2-thienyl)ethenyl-5-trifluoromethylbenzo[b]thiophene-2-carboxamide, m.p. 192°–194° C.

EXAMPLE 14

(S-oxidation)

3-Hydroxy-N-(2,2-dipheny)ethenyl-5-methylsulfinyl-benzo[b]thiophene-2-carboxamide A mixture of 3-hydroxy-5-methylthio-N-(2,2-diphenylethenyl)-benzo[b]thiophene-2-carboxamide (0.42 g, 0.0010 moles) and 30% $H_2O_2$ (0.80 ml) in acetic acid (10 ml) was stirred at 75° for 30 minutes. The reaction was cooled to 0° and the yellow precipitate was filtered, acetic acid washed and dried under vacuum, to afford 0.38 g (88%) of 3-hydroxy-N-(2,2-diphenyl)ethenyl-5-methylsulfinylbenzo[b]thiophene-2-carboxamide. MS gave Mol ion at 433.

Method D—Preparation of Common Intermediate

A convenient method for preparing the starting materials, e.g., a 3-hydroxybenzo[b]thiophene-2-carboxamide, is as described in the following scheme:

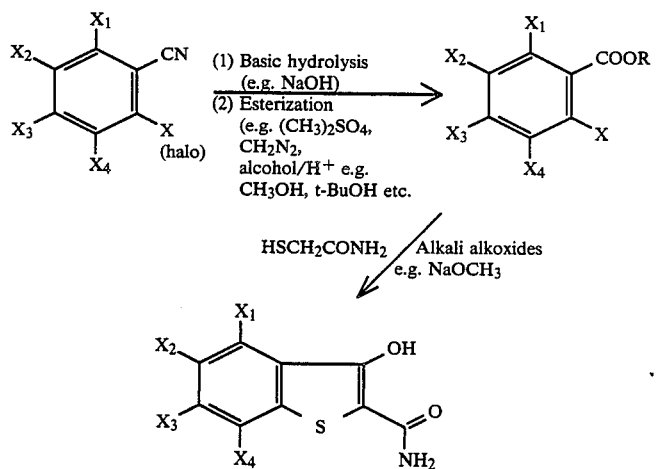

*wherein $R^o$ is $C_{1-6}$ alkyl benzyl or substituted benzyl.

EXAMPLE 15

3-Hydroxy-5-trifluoromethyl-benzo[b]thiophene-2-carboxamide

Step A: Preparation of 2-Chloro-5-trifluoromethylbenzoic acid

A solution of 570 g (2.77 moles) of 2-chloro-5-trifluoromethylbenzonitrile (1) and 1140 g (28.5 moles) NaOH in 2.3 L water was heated at reflux in a 12 L flask overnight. TLC (silica gel, 20% ethyl acetate-hexane with 1 drop acetic acid/10 ml solution) showed reaction was complete. The solution was cooled, diluted with 3.5 L ice water and extracted with 1 liter ether. The aqueous extract was cooled in an ice bath, acidified to pH 2 with cold 50% $H_2SO_4$ and extracted with four 1.3 liter portions of ether. The ether extracts were dried over $Na_2SO_4$ and evaporated and the residue was triturated with 1.2 liters hot hexane, cooled, and filtered to afford 615 g (9%) of 2-chloro-5-trifluoromethylbenzoic acid as white needles, m.p. 93°–94° C.

Anal. Calcd. for $C_8H_4O_2F_3Cl$: C, 42.79; H, 1.79; Cl, 15.79; F, 25.38.

Found: C, 42.73; H, 1.74; Cl, 15.43; F, 25.01.

Step B: Preparation of Methyl 2-chloro-5-trifluoromethylbenzoate

A sample of 620 g (3.25 moles) of tris-(2-hydroxypropyl)amine was melted on a steam bath. This was added slowly to a solution of 615 g (2.75 moles) of 2-chloro-5-trifluoromethylbenzoic acid and 375 g (282 ml, 2.98 moles) of dimethylsulfate in 750 ml of acetone in a 5 liter flask. (The solution began to boil during the course of the addition and was kept at 30° C. to 40° C. by intermittant cooling in an ice bath.) After addition was complete the solution was boiled on a steam bath for 30 minutes. The hot solution was diluted first with 250 ml water and, after 10 minutes, with 250 ml of 2N HCl and 750 ml of water and allowed to stir overnight. The solution was extracted with two 2 liter portions of dichloromethane and the organic extract was washed with saturated $K_2CO_3$ and water, dried over $Na_2SO_4$ and evaporated to afford 630 g (96%) of methyl 2-chloro-5-trifluoromethylbenzoate as a yellow liquid. TLC (silica gel, 10% $CH_2Cl_2$-hexane) showed 1 spot (ester at $R_f$ 0.4; this material was pure enough to be used in the next step without distillation. IR (NaCl, neat) 3080, 3000, 2960 (C—H), 1735 (C=O); NMR [$CDCl_3$, $(CH_3)_4Si$] 3.78 (s, 3H, $CH_3$—), 7.27 (d, 1H, H—3, $J_{3,4}=9$), 7.43 (d of d, 1H, H—4, $J_{3,4}=9$, $J_{4,6}=2.4$), 7.80 (d, 1H, $J_{4,6}=2.5$); Mass Spectrum: m/e 240, 238 (1:3, M+), 209, 207 (1:3, M—$OCH_3$), 181, 179 (1:3, M—$CO_{22}CH_3$). B.p. 95° C. at 4.5 torr.

Step C: Preparation of Mercaptoacetamide

One liter of methanol was cooled to 0° in a 3 liter flask and saturated with ammonia. Then 100 g (9.43 moles) of methyl thioglycolate (Aldrich Chemical Co.) was added carefully ($NH_3$ evolves) and the solution was stirred at room temperature for 48 hours while maintaining a constant stream of $NH_3$ through the solution. TLC (1:1 ether-hexane with 1 drop acetic acid/10 ml solution) showed complete reaction, with product at $R_f$ 0.2.

The solvent was evaporated to a white solid that was triturated with 1 liter 20% $CH_2Cl_2$-petroleum ether (b.p. 35°–60° ), filtered, and washed with 1 liter petroleum ether (b.p. 35°–60° ) to afford 848 g (99%) of mercaptoacetamide as white needles, m.p. 51°–52° C.

Anal. Calcd. for $C_2H_5NOS$: C, 26.40; H, 5.49; N, 15.35; S, 35.16.

Found: C, 26.45; H, 5.19; N, 15.35; S, 34.68.

Step D: Preparation of 3-Hydroxy-5-trifluoromethylbenzo[b]thiophene-2-carboxamide A solution of 320 g (3.5 moles) of 5 and 750 ml N,N-dimethylformamide was stirred in a 12 liter flask. Then 175 g (3.24 moles) of solid sodium methoxide was added in 5 portions (600 ml acetonitrile was added to prevent solidification) and the slurry was stirred for 10 minutes. A solution of 630 g (2.64 moles) of 3 in 500 ml acetonitrile was added and the mixture was stirred for 15 minutes. An additional 175 g (3.24 moles) of solid sodium methoxide and 200 ml of acetonitrile were added and the mixture was heated at reflux for 6 hours.

Separate additions of the sodium methoxide are necessary to prevent solidification of the reaction mixture.

TLC (silica gel, 1:1 ether-hexane with 1 drop acetic acid/10 ml) showed that cyclization was not complete ($R_f$ of product=0.4, $R_f$ of uncyclized ester=0.3, $R_f$ of thiol=0.2), so 500 ml of 12.5% sodium methoxide in methanol was added and the mixture was heated at reflux overnight.

The acetonitrile was evaporated and the mixture was cooled to 0° and diluted with 500 ml methanol and 2 liters cold 6 M HCl. After stirring for 30 minutes the mixture was diluted with 600 ml water, cooled to 0° and filtered. The residue was crystallized from 2:1 methanol-water and washed with carbon tetrachloride, then hexane to afford 575 g (83%) of 3-hydroxy-5-trifluoromethyl-benzo[b]thiophene-2-carboxamide as pale tan needles, m.p. 196°–197°.

Anal. Calcd. for $C_{10}H_6NO_2F_3S$: C, 45.98; H, 2.31; N, 5.36; F, 21.82; S, 12.27.

Found: C, 46.04; H, 2.30; N, 5,35; F, 12.24; S, 21.90.

The pharmaceutically acceptable salts of compounds of Formula I (at the 3-hydroxy site when R is H) are readily prepared by conventional procedures well-known in the art. For example, a compound of Formula I is treated with an appropriate amount of a base, such as an alkali or alkaline earth metal hydroxide, e.g. sodium hydroxide, potassium hydroxide, and calcium hydroxide or an organic base such as an alkoxide, e.g., $CH_3ONa$, t-BuOk, or the like.

The pharmaceutically acceptable esters of the phenol of formula (I) can also be prepared by conventional methods. For example, (1) a compound of Formula (I) is treated with an acyl halide such as acetylchloride or an acid anhydride such as acetic acid anhydride.

C. Utility of the compounds within the scope of the invention

This invention also relates to a method of treatment for patients (or mammalian animals raised in the dairy, meat, or fur industries or as pets) suffering from disorders or diseases mediated by prostaglandins and/or leukotrienes, and gastric irritation or lesion. More specifically, this invention is directed to a method of treatment involving the administration of one or more of the dual enzyme inhibitors of formula (I) as the active constituent.

Accordingly, a compound of Formula (I) can be used among other things to reduce pain and inflammation, to correct respiratory, cardiovascular, and intravascular alterations or disorders, and to regulate immediate hypersensitivity reactions that cause human asthma and allergic conditions.

For the treatment of inflammation, arthritis conditions, cardiovascular disorder, allergy, psoriasis, asthma, or other diseases mediated by prostaglandins and/or leukotrienes, a compound of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable prerarations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or algenic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethelcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid. Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed.

Dosage levels of the order of from about 0.01 mg to about 150 mg per kilogram of body weight per day are useful in the treatment of the above-indicated conditions (about 0.5 mg to about 7.5 gms. per patient per day). For example, inflammation may be effectively treated by the administration of from about 0.2 to 50 mg of the compound per kilogram of body weight per day (about 20 mg to about 3.5 gms per patient per day). Preferably a dosage of from about 1 mg to about 20 mg per kilogram of body weight per day may produce good results (about 25 mg to about 1 gm per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

Particularly, for use in treatment of ophthalmic conditions including those associated with elevated intraocular pressure such as glucoma or other inflammation in the eye. The active compound can be administered topically or systemically when it is appropriate. The dose administered can be from as little as 0.1 to 25 mg or more per day, singly, or preferably on a 2 to 4 dose per day regimen although a single dose per day is satisfactory.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof such as the sodium or potassium salt is formulated into an ophthalmic preparation. In such formulations, from 0.1% to 15% by weight can be employed. The objective is to administer a dose of from 0.1 to 10 mg per eye per day to the patient, with treatment continuing so long as the condition persists.

Thus, in an ophthalmic solution, insert, ointment or suspension for topical delivery, or a tablet, intramuscular, or intravenous composition for systemic delivery, the active medicament or an equivalent amount of a salt thereof is employed, the remainder being carrier, excipients, preservatives and the like as are customarily used in such compositions.

The active drugs of this invention are most suitably administered in the form of ophthalmic pharmaceutical compositions adapted for topical administration to the eye such as a suspension, ointment, or as a solid insert. Formulations of these compounds may contain from 0.01 to 15% and especially 0.5% to 2% of medicament. Higher dosages as, for example, about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

As with all medications, dosage requirements are variable and must be individualized on the basis of the disease and the response of the patient.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that either is soluble in lacrimal fluids, or otherwise disintegrates.

The following examples of ophthalmic formulations are given by way of illustration.

EXAMPLE 16

| | | |
|---|---|---|
| Compound A | 1 mg. | 15 mg. |
| Monobasic sodium phosphate.2H$_2$O | 10 mg. | 5 mg. |
| Dibasic sodium phosphate.12H$_2$O | 30 mg. | 15 mg. |
| Benzalkonium chloride | 0.1 mg. | 0.1 mg. |
| Water for injection q.s. ad. | 1.0 ml. | 1.0 ml. |

Compound A, phosphate buffer salts, and benzalkonium chloride are added to and dissolved in water. The pH of the composition is adjusted to 6.8 and diluted to volume. The composition is rendered sterile by ionizing radiation.

EXAMPLE 17

| | |
|---|---|
| A Compound of formula (I) | 5 mg. |
| petrolatum q.s. ad. | 1 gram |

The active compound and the petrolatum are aseptically combined.

EXAMPLE 18

| | |
|---|---|
| A Compound of formula (I) | 1 mg. |
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 19

| | |
|---|---|
| A Compound of formula (I) | 1 mg. |
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE 20

| A Compound of formula (I) | 1 mg. |
|---|---|
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE 21

| A Compound of formula (I) | 1 mg. |
|---|---|
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R. H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

EXAMPLE 22

The following materials are admixed in a 1250 ml bottle: 24 g of Compound A which is a sufficient amount of medicament to result in a concentration of 10 mg per ml in the final samples, allowing for previously established 3.0% average; 0.4 g sodium bisulfite, 12 g NaCl, and 28 ml water (at 180° F.). This mixture, (I), is autoclaved for 30 minutes at 121° C. under 15 psig. Separately, 3 g of hydroxyethylcellulose in 720 ml of water (II) and 0.4 g of lecithin in 80 ml of water (III) were autoclaved for 30 minutes at 121° C. Then, (III) is admixed with (I) for 2 hours, and the resultant mixture poured into (II). Another mixture (IV) is prepared from 20 g of sorbitol, 2.36 ml of benzalkonium chloride, 10 g of disodium edetate, and water to give a final solution volume of 900 ml. Then, (IV) is added to the mixture of (I), (II), and (III) in sufficient quantity to give 1.8 l. overall. The 1.8 l. mixture of I, II, III, and IV is then taken and homogenized using a homogenizer at 2000 psig. Stock solutions are then prepared for polyoxyethylene (20) sorbitan monooleate by dissolving 3 g of the material in 100 ml of water, and of benzyl alcohol/β-phenyl-ethyl alcohol by admixing 50 ml of each alcohol. Varying quantities of the two stock solutions are then added to four 90 ml aliquots of the homogenized mixture of (I), (II), (III), and (IV) prepared as described above, together with sufficient water to give a total of 100 ml for each of four different samples.

Other formulations, in an oil vehicle and an ointment are exemplified in the following examples.

EXAMPLE 23

Solution Composition

| Solution Composition | |
|---|---|
| 6-(2-Sulfamoylbenzo[b]thienyl) 2,2-dimethylpropionate | 0.1 mg. |
| Peanut oil q.s. ad. | 0.10 mg. |

The solution is rendered sterile by filtration through a sterilizing filter.

EXAMPLE 24

| 6-(2-Sulfamoylbenzo[b]thienyl) cyclopentaneacetate | 0.5 gm. |
|---|---|
| Petrolatum q.s. ad. | 1 gram |

The compound and the petrolatum are aseptically combined.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

D. Biological Data Supporting the Utility of the Compound Within the Scope of the Invention The following is a summary of biological data from three standard bioassays. These data serve to illustrate that the compound of formula (I), e.g., 3-hydroxy-5-trifluoromethyl-N-[2-phenyl-2-(2-thienyl)]benzo[b]thiophene-2-carboxamide (hereinafter referred to as compound A), are (1) dual cyclooxygenase/lipoxygenase inhibitors useful as anti-inflammatory, analgesic and antipyretic agents; and (2) cytoprotective agents useful in the prevention or treatment of gastric irritation and lesions.

1. Platelet Activating Factor. Induced Hyperalgesia in the Rat.

In this assay, which is sensitive to inhibition by lipoxygenase inhibitors but not cyclooxygenase inhibitors, compound A markedly reduced the pain response to PAF ($ED_{50}$ 0.19 mg/kg p.o.) (Table 1). Indomethacin, ibuprofen, piroxicam, and benoxaprofen were completely ineffective in this assay (Table 2).

Groups of 10 female Sprague-Dawley rats, 35–50 g (Taconic Farms), were fasted overnight prior to testing. Hyperalgesia was induced in the rat by the subplantar injection of 1 ug PAF in physiological saline. Pain threshold was measured by applying pressure to the plantar surface of the hindpaw by means of a compressed air driven piston with a 2 mm tip. Vocalization thresholds were obtained 3 hr after injection of the PAF. Compounds, prepared at various doses in 1% methylcellulose suspension, were administered perorally 30 min before PAF. For each drug treatment group, animals with response pressures in the inflamed paw of 200% of control was considered to be analgesic. The mean vocalization threshold for each group was also calculated. The $ED_{50}$ and 95% confidence limits were calculated by regression analysis.

TABLE 1

Effect of Compound A on PAF-Induced Hyperalgesia in the Rat

| Treatment | Dose (mg/kg p.o.)[a] | N | Vocalization Threshold[b] | % Analgesia[c] |
|---|---|---|---|---|
| Vehicle | — | 30 | 9.1 | — |
|  | 0.001 | 10 | 10.2 | 10 |
| Compound A | 0.01 | 20 | 13.3 | 25 |
|  | 0.03 | 20 | 13.0 | 30 |
|  | 0.1 | 30 | 16.9 | 50 |
|  | 0.3 | 20 | 17.6 | 50 |
|  | 1.0 | 30 | 20.1 | 67 |
|  | 3.0 | 20 | 18.3 | 70 |
| $ED_{50}$[d] (confidence limits) |  |  | 0.19 mg/kg (0.11–0.3) |  |

[a]Drug administered 30 min before PAF.
[b]Mean mmHg in the inflamed paw. Reading taken 3 hr after PAF. Mean V.T. in the contralateral paw was 21.7 mmHg.
[c]Percentage of animals with V.T. greater than 200% of vehicle-treated controls.
[d]$ED_{50}$ calculated as dose required to raise VT to greater than 200% of vehicle-treated control in 50% of animals.

TABLE 2

Effect of Compound A and Standard Cyclooxygenase Inhibitors in the PAF-induced Hyperalgesia Assay in the Rat

| Test Substance | Dose mg/kg p.o. | % Rats Exhibiting Analgesia |
|---|---|---|
| Compound A | 0.1 | 50 |
| Indomethacin | 10 | 10 |
| Piroxicam | 30 | 0 |
| Ibuprofen | 30 | 10 |
| Sulindac | 30 | 10 |
| Diflunisal | 30 | 10 |
| Aspirin | 100 | 10 |
| Naproxen | 30 | 10 |
| Benoxaprofen | 30 | 10 |

2. PHENYLBENZOQUINONE (PBQ)—induced writhing in the Mouse

In this assay which is sensitive to inhibition by cyclooxygenase but not lipoxygenase inhibitors, Compound A effectively inhibited PBQ-induced writhing ($ED_{50}$ 1 mg/kg p.o.) (Table 3). The analgesic activity of Compound A was equivalent to piroxicam and greater than ibuprofen.

Groups of 10 female mice (CD-1, Charles River Breeding Laboratories), weighing 20-25 g were fasted overnight prior to experiments. Test substances, suspended in 1% methylcellulose, were administered orally 60 minutes prior to the intraperitoneal administration of PBQ (10 ml/kg of 0.02% solution). The mice were placed in individual boxes and exactly 5 minutes later were observed for "writhes" (abdominal contractions, lordosis, and hindlimb extension) for a 10 minute interval as a measure of pain induction. The number of writhes for each animal was recorded and the group means and standard errors were calculated. The means obtained from the drug treated groups were compared to the vehicle control means values and percent inhibition of writhing was calculated. $ED_{50}$ values were calculated by regression analysis.

TABLE 3

The Effects of Compound A and Standard Drugs In the Phenylbenzoquinone Writhing Assay in the Mouse

| Test Substance[a] | Dose mg/kg p.o. | N | % Inhibition | $ED_{50}$ |
|---|---|---|---|---|
| Compound A | 0.1 | 60 | 9 ± 3 | 1.0 |
|  | 0.3 | 70 | 10 ± 5 | $CL^c$ (0.3–4.0) |
|  | 1.0 | 60 | 39 ± 13 |  |
|  | 3.0 | 80 | 78 ± 7 |  |
| Ibuprofen |  |  |  | 9.0 |
| Piroxicam |  |  |  | 2.0 |

[a]Administered 1 hr before PBQ injection.
[b]N.E.—no effect at 30 mg/kg.
[c]confidence level.

3. Adjuvant Arthritis Assay

In the chronic (21 days), developing adjuvant-arthritis assay in the rat, Compound A evoked marked inhibition of swelling of the noninjected hindpaw. Table 4 shows that the $ED_{50}$ of Compound A at day 14 was 3.0 mg/kg and was still active at days 21 with an $ED_{50}$ of 10 mg/kg. X-ray analysis of the hindpaw joints of these animals on day 21 showed that protection of the bone and cartilage destruction was only seen at the 10 mg/kg day dose level. Indomethacin at a dose level of 1 mg/kg day provided virtually complete protection from hard tissue destruction. During the development of adjuvant arthritis, the rats lose body weight, the thymus gland involutes and the adrenal gland weight increases. At both dose levels, Compound A significantly inhibited body weight loss (although the animals still showed a net loss of body weight), and at 10 mg/kg/day inhibited the loss in weight of the thymus (Table 5).

Female Lewis rats (purchased from Charles River, Wilmington, MA) were sorted into groups of ten in the weight range 160 - 199g. The rats were sensitized to *Mycobacterium butyricum* (Difco) by the subplantar injection of 0.1 ml light mineral oil (Lubinol, Purepac Pharmaceutical Co., Elizabeth, NJ) containing 0.5 mg of the *Mycobacterium* into the left hindpaw. The *Mycobacterium* suspension was prepared by grinding in a glass mortar followed by the addition of the appropriate volume of light mineral oil. The suspension was transferred to a glass vial and stirred for 15 minutes on a magnetic stirrer to obtain a uniform suspension. After sensitization the rats were returned to metronic wire-bottomed cages and allowed food and water ad libitum with the food placed on the bottom of the cages for easy access. Using this protocol, evidence of systemic involvement (swelling of the contralateral hindpaw) was seen 12-14 days after sensitization. Rats received compound daily perorally as a suspension in 0.25% agar starting on the day of sensitization. Disease was quantitated by measuring the volume of the noninjected hindpaw by mercury displacement on days 0, 14 and 21. On day 21 (at the termination of the experiment) x-rays of the noninjected hindpaw were taken using a Phillips dental x-ray machine. Total body weight was determined on days 0 and 21 and at the termination of the experiment the thymus was removed and weighed. The statistical significance of the data was determined using Students t test.

TABLE 4

Effect of Compound A and Indomethacin in the Developing Adjuvant-Induced Arthritis Assay in the Lewis Rat

| Treatment | Dose mg/kg/day P.O. | N | % Inhibition+ Foot Swelling-Day 14 (e liters) | % Inhibition+ Foot Swelling-Day 21 | Bone/Cartilage++ Destruction Score |
|---|---|---|---|---|---|
| Control | — | 10 | 1025 ± 127 | 1617 ± 130 | 2.7 |
| Compound A | 3.0 | 10 | 449 ± 83 (56%)* | 921 ± 125 (43%)* | 2.6 |
| Compound A | 10.0 | 10 | 279 ± 39 (73%) | 554 ± 67 (66%) | 1.1 |
| Indomethacin | 1.0 | 10 | 132 ± 54 (87%)* | 190 ± 38 (88%)* | 0.1 0.1 |

Mean ± SEM
*Statistically significant P 0.05 Assessed subjectively on a score 0–3, 0 = 0 destruction, 3 = Maximum destruction.

TABLE 5

Effect of Compound A on Body Weight, Thymus Weight and Adrenal Weight in the Developing Adjuvant-Induced Arthritis Assay in the Rat

| Compound | Dose mg/kg/day P.O. | N | Change Body Weight 0–21 days (gm) | Thymus Weight (mg) | Adrenal Weight (mg) |
|---|---|---|---|---|---|
| Control | — | 10 | −20.9 ± 1.4 | 158.3 ± 6.6 | 92.4 ± 1.9 |
| Compound A | 3.0 | 10 | −14.7 ± 3.2* | 161.0 ± 17.7 | 74.6 ± 3.3 |
| Compound A | 10.0 | 10 | −12.2 ± 2.9* | 241.5 ± 17.1* | 91.8 ± 2.7 |
| Indomethacin | 1.0 | 10 | 0.7 ± 3.4* | 359.6 ± 17.9* | 82.7 ± 2.8 |

Mean ± SEM
*Statistically different from control P 0.05 Weight (mg) non-adjuvant treated adrenals = 81.7 ± 3.7

4. Cytoprotection Assay

Male Sprague-Dawley rats, 130–150 g each, were sorted into groups for assay. The rats were fasted for 24 hours. Ulcers were then induced by peroral administration of indomethacin (10 mg/kg) in 0.5% methyl cellulose, and compound A in 0.5% methylcellulose was perorally administered.

Several hours after the administration of compound A, the animals are sacrificed, the stomachs removed, excises along the inner curvature, washed carefully with cool tap water and placed in 0.9% saline. When all groups have been processed, the mucosal region of the stomachs are examined under a magnifying lens and scored according to the total number of lesions present. Group scores represent the mean score of animals in that group. The effect of Compound A on indomethacin-induced gastric lesions is shown below in Table 6:

TABLE 6

The Effect of the Dual Inhibitor, Compound A on Indomethacin-Induced Gastric Lesions In the Rat

| | Dose mg/kg P.O. | N | No. Gastric Lesions (Mean + S.E.M.) | % Inhibition of Lesions |
|---|---|---|---|---|
| Indomethacin | 10.0 | 18 | 12.6 ± 4.4 | — |
| Compound A | 0.1 | 15 | 6.7 ± 4.1 | 47 |
| " | 0.3 | 15 | 5.0 ± 3.1 | 60 |
| " | 1.0 | 15 | 6.1 ± 5.5 | 52 |
| " | 10.0 | 15 | 2.4 ± 1.1 | 81 |

What is claimed is:
1. A compound of formula

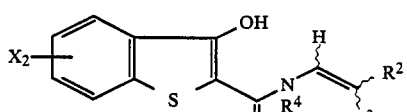

or a pharmaceutically acceptable salt thereof wherein:
$R^2$ and $R^3$ independently are
 (a) phenyl of formula

wherein $X_5$ and $X_6$ independently are
 (1) Q where Q is H, loweralkyl or haloloweralkyl;
 (2) halo;
 (3) SQ;
 (4) OQ; or
 (5) SOQ;
 (b) thienyl of formula

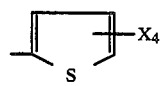

wherein $X_4$ represents Q or halo;
$R^4$ is H or loweralkyl; and
$X_2$ is
 (a) Q;
 (b) halo;
 (c) OQ;
 (d) phenyl;
 (e) 5-(2,4-difluorophenyl);
 (f) SQ; or
 (g) $CF_3CONH-$.

2. A pharmaceutical composition for treating inflammation, fever and pain in a mammalian species comprising a pharmaceutically acceptable carrier and an effective amount of a compound of formula

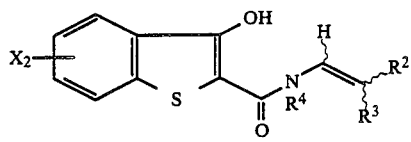

or a pharmaceutically acceptable salt thereof wherein:
$R^2$ and $R^3$ independently are
(a) phenyl of formula

wherein $X_5$ and $X_6$ independently are
(1) Q where Q is H, loweralkyl or haloloweralkyl;
(2) halo;
(3) SQ;
(4) OQ;
(5) SOQ; or
(b) thienyl of formula

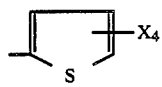

wherein $X_4$ represents Q or halo;
$R^4$ is H or loweralkyl; and
$x_2$ is
(a) Q;
(b) halo;
(c) OQ;
(d) phenyl;
(e) 5-(2,4-difluorophenyl);
(f) SQ; or
(g) $CF_3CONH—$.

3. The compound of claim 1 which is 3-hydroxy-5-trifluoromethyl-N-(2-phenyl-2-(2-thienyl)ethenyl)-benzo(b)thiophene-2-carboxamide or a pharmaceutical salt thereof.

4. The pharmaceutical composition of claim 2 wherein the compound is 3-hydroxy-5-trifluoromethyl-N-(2-phenyl-2-(2-thienyl)ethenyl) benzo(b)thiophen-2-carboxamide or a pharmaceutical salt thereof.

* * * * *